United States Patent [19]
Pond et al.

[11] Patent Number: 4,465,854
[45] Date of Patent: Aug. 14, 1984

[54] PREPARATION OF ETHYL ACETATE

[75] Inventors: David M. Pond; Thomas J. Glenn, both of Kingsport, Tenn.

[73] Assignee: Eastman Kodak Company, Rochester, N.Y.

[21] Appl. No.: 244,578

[22] Filed: Mar. 17, 1981

[51] Int. Cl.³ .................... C07C 67/00; C07C 67/297; C07C 69/14
[52] U.S. Cl. ..................................... 560/265; 562/607
[58] Field of Search ......................................... 560/265

[56] References Cited

U.S. PATENT DOCUMENTS

| 3,579,566 | 5/1971 | Fenton | 560/263 |
| 3,957,827 | 5/1976 | Lyons | 560/265 |
| 4,221,918 | 9/1980 | Suzuki | 560/263 |

Primary Examiner—Vivian Garner
Attorney, Agent, or Firm—David E. Cotey; Daniel B. Reece, III

[57] ABSTRACT

Process for the preparation of ethyl acetate by hydrogenating acetic anhydride in the presence of a Raney nickel catalyst. The process can also be utilized to hydrogenate mixtures of acetic anhydride and ethylidene diacetate to produce ethyl acetate.

6 Claims, No Drawings

PREPARATION OF ETHYL ACETATE

This invention relates to a novel process for the preparation of ethyl acetate by hydrogenating acetic anhydride. The invention also relates to a novel process for hydrogenating mixtures of acetic anhydride and ethylidene diacetate to obtain ethyl acetate.

An economically advantageous process for the preparation of acetic anhydride by the carbonylation of methyl acetate has been reported in the patent literature. See, for example, Belgian Pat. No. 819,455, British Published Patent Application No. 2,103,184, Japanese Published Patent Applications Nos. 75-47921 and 75-47922 and U.S. Pat. Nos. 3,927,078 and 4,046,807. Not only is acetic anhydride itself an important chemical, for example as an acetylating agent in the manufacture of cellulose acetate and other esters, but it can be converted to ethyl acetate which presently is derived primarily from petroleum or natural gas.

The hydrogenation of acetic anhydride using a nickel catalyst in the presence of a strong acid, i.e., HCl, HF, or methane sulfonic acid, is disclosed in U.S. Pat. No. 4,221,918. The products obtained are reported to be ethylidene diacetate, acetic acid and, when HCl was the acid used, 1-chloroethyl acetate.

The process of this invention comprises hydrogenating at elevated pressure and temperature acetic anhydride in the presence of a catalytic amount of a Raney nickel catalyst. The process also can be used to convert mixtures of acetic anhydride and ethylidene diacetate, resulting from the carbonylation of methyl acetate in the presence of hydrogen, to ethyl acetate. The feed to the hydrogenation reactor can, if desired, contain, in addition to acetic anhydride and/or ethylidene diacetate, an inert solvent such as acetic acid. The co-product acetic acid may be converted to methyl acetate and used in the production of acetic anhydride.

Using appropriate conditions, acetic anhydride containing little if any ethylidene diacetate, e.g. up to about 10 weight percent, is readily hydrogenated to produce ethyl acetate in good product and space-time yields with the formation of essentially no ethylidene diacetate. However, it has been found that the presence of larger amounts of ethylidene diacetate inhibits the conversion of acetic anhydride to products and thus, the use of more severe reaction conditions is necessary to satisfactorily hydrogenate mixtures of acetic anhydride and ethylidene diacetate. Such reaction conditions are also necessary to effect hydrogenation at least a portion of the ethylidene diacetate.

The concentration of the Raney nickel can be varied substantially depending on such factors as the temperature and pressure employed, the material being hydrogenated, the product and/or space-time yeild desired, capability to dissipate the heat of reaction, etc. Generally, concentrations in the range of about 0.1 to 10 weight percent, based on the acetic anhydride and, when present, ethylidene diacetate fed, will give good results when using appropriate pressures and temperatures. Catalyst concentrations (same basis) of about 0.5 to 2.5 weight percent will most often be used.

The hydrogenation-effective temperatures and pressures employed in the process of this invention also can be varied. Temperatures in the range of about 100° to 250° C. may be used although at the higher temperatures ethyl acetate decomposition will tend to be a problem. Pressures (total reaction pressure) in the range of about 500 to 5000 psig may be used, although the use of pressures in excess of 2500 psig normally is not advantageous. The preferred temperatures and pressures vary depending on whether the material being hydrogenated consists primarily of acetic anhydride or consists of a mixture of acetic anhydride and ethylidene diacetate, e.g. mixtures of acetic anhydride and ethylidene diacetate in weight ratios of about 4:1 to 1:4. When the material being hydrogenated consists primarily of acetic anhydride, the preferred temperatures and pressures are in the range of about 130° to 200° C., especially 130° to 150° C., and about 500 to 1500 psig. When the material is a mixture of acetic anhydride and ethylidene diacetate, preferred temperatures and pressures are about 170° to 250° C., especially 200° to 225° C., and about 2000 to 2500 psig.

The process of the invention may be carried out as a batch operation or, more suitably, as a continuous process wherein acetic anhydride and/or ethylidene diacetate is continuously fed to an autoclave-like reactor and reaction mixture containing the desired products is continuously removed, e.g. as a liquid via a filter leg or by vapor take-off means. Unreacted materials and co-product acetic acid may be removed from the reactor take-off, for example, in a distillation train, and recycled to the reactor.

The process of the invention is further illustrated by the following examples.

EXAMPLES 1–18

Acetic anhydride (100 g.) and mixtures of acetic anhydride (50 g.) and ethylidene diacetate (50 g.) were hydrogenated in the presence of varying amounts of Raney nickel using different temperatures and total autoclave pressures. The material hydrogenated in Examples 1–7 was acetic anhydride and in Examples 8–18 it was the 50-50 mixture. W. R. Grace Raney nickel No. 28 was used in all of the examples except in Example 18 wherein the nickel catalyst used was DEGUSSA Raney B-313. The acetic anhydride, ethylidene diacetate (when used) and Raney nickel catalyst were loaded into a 300 ml. Hastalloy B autoclave designed to operate in a rocking mode. The autoclave was purged with 100 psig hydrogen gas pressure at room temperature and then the gas was vented. The autoclave internal pressure was increased to 10 psig by adding hydrogen gas at room temperature. The autoclave was sealed and heated and rocked until reaction temperature was reached, at which time additional hydrogen gas was added to increase the autoclave internal pressure to the predetermined value. The time at which the autoclave internal pressure reached the predetermined value was taken as the start of the reaction time. A 2 hour reaction time was used in Examples 1–16 and 1 hour in Examples 17 and 18. Reactor pressure was maintained at the preset value during the experiment by adding hydrogen gas at the same rate at which it was consumed by the reactants. When the predetermined reaction time was completed the autoclave was cooled by a stream of cold air. After the gas was vented from the autoclave the reaction product was analyzed by gas chromatographic methods.

Table I shows the temperature (°C.) and pressure (psig) used, the amount of catalyst (cat., g.) charged, the amount (in moles) of ethyl acetate (EA) produced, the percent of acetic anhydride ($Ac_2O$) and ethylidene diacetate (EDA) consumed (cons.) and the product yield (PY, percent of theory) and space-time yields (STY, in grams/liter liquid-hour) for ethyl acetate.

TABLE I

| Ex. | Cat. | Temp. | Press. | EA | Ac$_2$O Cons. | EDA Cons. | EA PY | EA STY |
|---|---|---|---|---|---|---|---|---|
| 1 | 1.5 | 170 | 1000 | .42 | 97.8 | — | 87.5 | 185 |
| 2 | 2.5 | 140 | 500 | .33 | 78.6 | — | 85.7 | 145 |
| 3 | 0.5 | 140 | 1500 | .37 | 80.6 | — | 94.8 | 163 |
| 4 | 2.5 | 140 | 1500 | .35 | 89.0 | — | 80.5 | 154 |
| 5 | 0.5 | 200 | 1500 | .40 | 99.0 | — | 82.5 | 176 |
| 6 | 2.5 | 200 | 1500 | .32 | 100.0 | — | 65.3 | 141 |
| 7 | 0.5 | 140 | 500 | .21 | 46.9 | — | 91.3 | 92 |
| 8 | 1.5 | 190 | 1500 | .20 | 77.6 | 32.4 | 66.6 | 88 |
| 9 | 2.5 | 170 | 750 | .20 | 91.8 | 11.8 | 75.4 | 88 |
| 10 | 0.5 | 210 | 750 | .13 | 36.7 | 55.9 | 46.4 | 57 |
| 11 | 0.5 | 170 | 2250 | .12 | 46.9 | 8.8 | 82.7 | 53 |
| 12 | 2.5 | 210 | 750 | .21 | 67.4 | 76.5 | 49.4 | 92 |
| 13 | 2.5 | 170 | 2250 | .25 | 100.0 | 17.6 | 82.0 | 110 |
| 14 | 0.5 | 210 | 2250 | .43 | 98.0 | 79.4 | 84.3 | 189 |
| 15 | 2.5 | 210 | 2250 | .43 | 100.0 | 85.3 | 80.4 | 189 |
| 16 | 0.5 | 170 | 750 | .09 | 26.5 | 50.0 | 38.4 | 40 |
| 17 | 2.0 | 200 | 2000 | .35 | 100.0 | 55.0 | 80.8 | 308 |
| 18 | 2.0 | 200 | 2000 | .22 | 96.3 | 21.8 | 69.4 | 194 |

Although the invention has been described in considerable detail with particular reference to certain preferred embodiments thereof, variations and modifications can be effected within the spirit and scope of the invention.

We claim:

1. Process for the preparation of ethyl acetate which comprises hydrogenating at a temperature of about 100° to 250° C. and a pressure of about 500 to 5000 psig acetic anhydride or a mixture thereof with ethylidene diacetate in the presence of a catalytic amount of a Raney nickel catalyst and in the absence of strong protonic acid.

2. Process according to claim 1 wherein the catalyst concentration is about 0.1 to 10 weight percent based on the weight of the acetic anhydride and, if present, ethylidene diacetate.

3. Process according to claim 1 for the preparation of ethyl acetate which comprises hydrogenating acetic anhydride at a pressure of about 500 to 1500 psig and a temperature of about 130° to 200° C. in the presence of a catalytic amount of a Raney nickel catalyst and in the absence of strong protonic acid.

4. Process according to claim 3 wherein the catalyst concentration is about 0.5 to 2.5 weight percent based on the acetic anhydride and the temperature is about 130° to 150° C.

5. Process according to claim 1 for the preparation of ethyl acetate which comprises hydrogenating at a pressure of about 2000 to 2500 psig and a temperature of about 170° to 250° C. a mixture of acetic anhydride and ethylidene diacetate in the presence of a catalytic amount of a Raney nickel catalyst and in the absence of strong protonic acid.

6. Process according to claim 5 wherein the catalyst concentration is about 0.5 to 2.5 weight percent based upon the acetic anhydride and ethylidene diacetate and the temperature is about 200° to 225° C.

* * * * *